(12) United States Patent
Chenaux

(10) Patent No.: US 10,492,927 B2
(45) Date of Patent: Dec. 3, 2019

(54) CUP IMPACTOR

(71) Applicant: Incipio Devices SA, St-Blaise (CH)

(72) Inventor: Fabrice Chenaux, Cortaillod (CH)

(73) Assignee: Incipio Devices SA, St. Blaise (CH)

( * ) Notice: Subject to any disclaimer, the term of this patent is extended or adjusted under 35 U.S.C. 154(b) by 350 days.

(21) Appl. No.: 15/517,238

(22) PCT Filed: Oct. 12, 2015

(86) PCT No.: PCT/IB2015/001864
§ 371 (c)(1),
(2) Date: Apr. 6, 2017

(87) PCT Pub. No.: WO2016/055851
PCT Pub. Date: Apr. 14, 2016

(65) Prior Publication Data
US 2017/0304078 A1    Oct. 26, 2017
US 2018/0147069 A9    May 31, 2018

Related U.S. Application Data

(60) Provisional application No. 62/062,166, filed on Oct. 10, 2014.

(51) Int. Cl.
*A61B 17/58* (2006.01)
*A61B 17/60* (2006.01)
(Continued)

(52) U.S. Cl.
CPC .............. *A61F 2/4609* (2013.01); *A61F 2/34* (2013.01); *A61F 2002/30329* (2013.01); *A61F 2002/30535* (2013.01)

(58) Field of Classification Search
CPC combination set(s) only.
See application file for complete search history.

(56) References Cited

U.S. PATENT DOCUMENTS 6,626,913 B1    9/2003    McKinnon et al.
2008/0021481 A1*  1/2008    Burgi .................... A61F 2/4609
                                                        606/99

(Continued)

OTHER PUBLICATIONS

International Search Report, International patent application No. PCT/IB2015/001864; dated Oct. 12, 2015.

*Primary Examiner* — Sameh R Boles
(74) *Attorney, Agent, or Firm* — Da Vinci Partners LLC; John Moetteli

(57) ABSTRACT

A cup impactor (1, 1', 1") is provided, adapted to assist a surgeon in controlling implantation of a cup prosthesis (9). The impactor has an impactor body (8), a drive train assembly (71), an impactor nose (38), and a clamping handle (5). The impactor body (8) has on its proximal end, an impaction plate (7) connected thereto, and an impactor handle (6) formed thereon for handling by the surgeon and, on the distal end, an impactor cup support portion (8a) having a receiver recess (8b) therein. A drive train assembly (71) has a prosthesis engaging interface (11) at a distal end thereof, and a proximal end on which a positioning knob (2) is formed. The assembly (71) received and rotatably mounted in the receiver recess (8b) of the body (8) so as to expose the prosthesis engaging surface (11). An impactor nose (38) mounts on the distal end of the impactor body (8), through which the prosthesis engaging interface (11) extends. A clamping handle (5) pulls distal portion of the drive train assembly (71) and therefore any cup prosthesis (9) attached to the engaging interface (11) against the impactor nose (38) so as not to strain the proximal end of the drive train assembly (71).

16 Claims, 12 Drawing Sheets

(51) Int. Cl.
  *A61F 2/00* (2006.01)
  *A61F 2/46* (2006.01)
  *A61F 2/34* (2006.01)
  *A61F 2/30* (2006.01)

(56) References Cited

U.S. PATENT DOCUMENTS

2013/0226186 A1  8/2013 Burgi
2014/0081283 A1  3/2014 Liang

\* cited by examiner

CUP IMPACTOR

CROSS REFERENCE TO RELATED APPLICATIONS

This application is the National Stage of International Application No. PCT/IB2015/001864, filed Oct. 12, 2015, which claims benefit under 35 USC § 119(a), to U.S. provisional patent application Ser. No. 62/062,166, filed Oct. 10, 2014.

COPYRIGHT & LEGAL NOTICE

A portion of the disclosure of this patent document contains material which is subject to copyright protection. The Applicant has no objection to the facsimile reproduction by anyone of the patent document or the patent disclosure as it appears in the Patent and Trademark Office patent file or records, but otherwise reserves all copyright rights whatsoever. Further, no references to third party patents or articles made herein is to be construed as an admission that the present invention is not entitled to antedate such material by virtue of prior invention.

FIELD OF THE INVENTION

This invention relates to a surgical cup impactor, method, kit, surgical system and surgical apparatus for use in inserting a cup prosthesis in a bone cavity. The invention has particular application to a surgical impactor for accurately inserting a cup prosthesis in a prepared enlarged and shaped cavity within a bone.

BACKGROUND OF THE INVENTION

Surgical cup impactors exist in the art that assist a surgeon in controlling implantation of a cup prosthesis. A typical impactor has an impactor body, a drive train assembly, an impactor nose, and a clamping handle. The impactor body has on its proximal end, an impaction plate connected thereto, and an impactor handle formed thereon for handling by the surgeon and, on the distal end, an impactor cup support portion having a receiver recess therein. A drive train assembly used in such an impactor typically has a prosthesis engaging interface at a distal end thereof, and a proximal end on which a positioning knob is formed. The assembly is typically received and rotatably mounted in the receiver recess of the body so as to expose the prosthesis engaging surface through an impactor nose. A clamping handle pulls the proximal portion of the drive train assembly and, because the cup prosthesis is engaged with the engaging interface, clamps any cup prosthesis attached to the engaging interface against the impactor nose so as not to strain the proximal end of the drive train assembly. Typically, therefore, the entire drive train is pulled by the clamping handle, which results in considerable strain. The universal joint often fails due to this strain, which may result in inconvenience to the patient via complications in the surgical procedure.

What is needed therefore is a means which prevents the pulling on the universal joint or universal joints of the drive train assembly in order to promote the reliability and durability of the tool and thereby minimize complications to the patient.

SUMMARY OF THE INVENTION

A cup impactor is provided, adapted to assist a surgeon in controlling implantation of a cup prosthesis. The impactor has an impactor body, a drive train assembly, an impactor nose, and a clamping handle. The impactor body has on its proximal end, an impaction plate connected thereto, and an impactor handle formed thereon for handling by the surgeon and, on the distal end, an impactor cup support portion having a receiver recess therein. A drive train assembly has a prosthesis engaging interface at a distal end thereof, and a proximal end on which a positioning knob is formed. The assembly is received and rotatably mounted in the receiver recess of the body so as to expose the prosthesis engaging surface. An impactor nose mounts on the distal end of the impactor body, through which the prosthesis engaging interface extends. A clamping handle pulls distal portion of the drive train assembly and therefore any cup prosthesis attached to the engaging interface against the impactor nose so as not to strain the proximal end of the drive train assembly.

Those skilled in the art will appreciate that elements in the Figures are illustrated for simplicity and clarity and have not necessarily been drawn to scale. For example, dimensions may be exaggerated relative to other elements to help improve understanding of the invention and its variants. Furthermore, when the terms 'first', 'second', and the like are used herein, their use is intended for distinguishing between similar elements and not necessarily for describing a sequential or chronological order. Moreover, relative terms like 'front', 'back', 'top' and 'bottom', and the like in the Description and/or in the claims are not necessarily used for describing exclusive relative position. Those skilled in the art will therefore understand that such terms may be interchangeable with other terms, and that the variants described herein are capable of operating in other orientations than those explicitly illustrated or otherwise described.

DETAILED DESCRIPTION OF THE PREFERRED EMBODIMENT(S)

The following description is not intended to limit the scope of the invention in any way as they are exemplary in nature, serving to describe the best mode of the invention known the inventors as of the filing date hereof. Consequently, changes may be made in the arrangement and/or function of any of the elements described in the exemplary variants disclosed herein without departing from the spirit and scope of the invention. Specifically, although the invention, kit and method herein described is presented in the form of an acetabular cup impactor, this disclosure should not be interpreted as being limited thereto.

Figure 1:
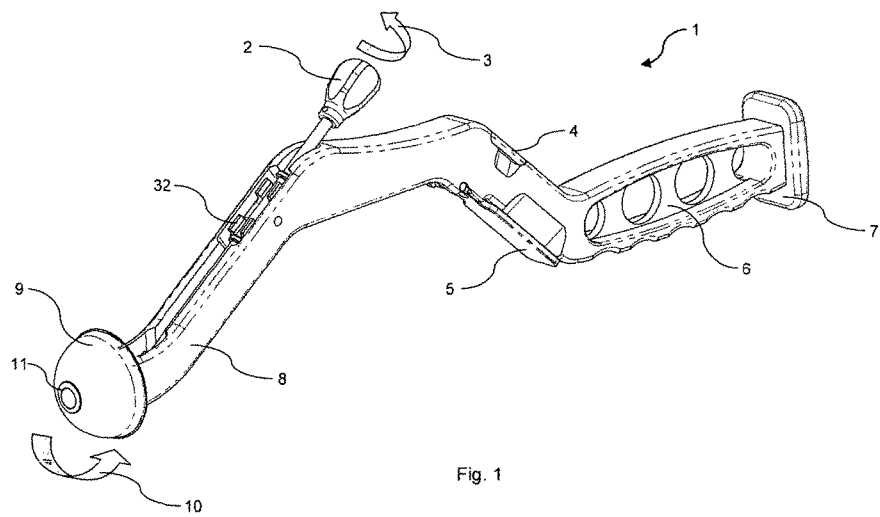
FIG. 1 is a perspective view of the preferred embodiment of the cup impactor, typically an acetabular cup impactor of the invention.
Figure 2:
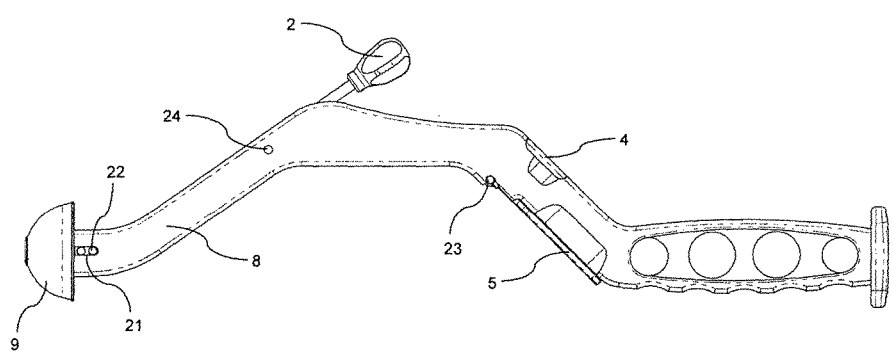
FIG. 2 is a side view of the preferred embodiment of the acetabular cup impactor.

Referring to FIGS. 1 and 2, an acetabular cup impactor 1 is provided to assist the surgeon in controlling the implantation of an acetabular cup prosthesis 9. The acetabular cup impactor 1 comprises an impactor body 8 having on its proximal end an impaction plate 7 fixedly connected to it. Openings and grooves are made in the proximal end of the impactor body 8, below the impaction plate, to form the impactor handle 6 and accommodate the handling of the instrument by the surgeon's hand. Note that further openings and grooves 100 are added to facilitate cleaning and sterilization.

The distal end of the cup impactor has a prosthesis engaging interface 11 (preferably threaded) located on the distal end of a drive train. A positioning knob 2 attached to the proximal end of a drive train allows rotation of it and therefore rotation of the cup prosthesis 9. Both proximal and distal ends of the drive train are linked together by a universal joint 34. The drive train assembly 71 is enclosed and maintained into the impactor body 8 by the drive train bearing 32. A clamping handle 5 allows the locking of the distal end of the drive train and therefore securing the acetabular cup prosthesis 9 against the impactor body 8. When the clamping handle 5 is in the open position, rotation (3) of the positioning knob 3 rotates (10) the acetabular cup prosthesis 9. As described below with more details, the release handle actuator 4 allows disassembling of the clamping handle 5 for easier cleaning and sterilization of the instrument.

In the preferred embodiment, the impactor body 8 may be C-shaped in order to minimize the invasiveness of the surgery by clearing anatomical structures. The axis of the impactor handle 6 is approximately aligned with the axis of the prosthesis engaging interface 11. It will be noted that different shape of the impactor body 8 and different offset (width of the C-shape) may be used without deviating from the scope of the present invention.

Figure 3:
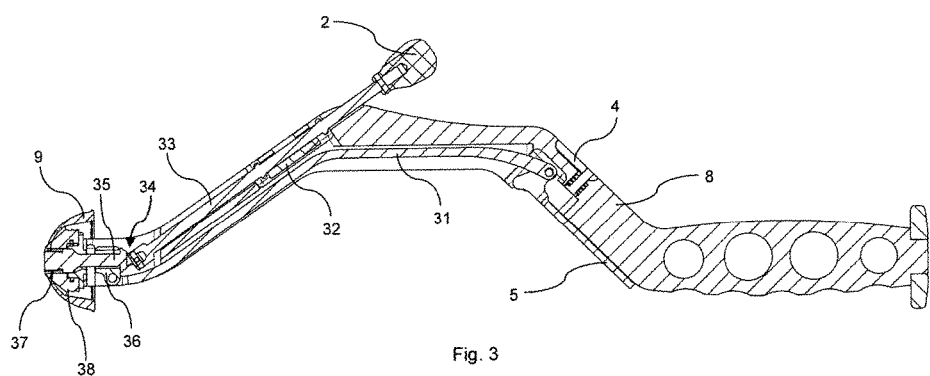
FIG. 3 is a cross-section view of the acetabular cup impactor in the clamped position.

Now referring to the FIG. 3, the cross-section view of the acetabular cup impactor is shown in the clamped position. The distal drive train shaft 35 has a threaded tip 37 here shown with an acetabular cup prosthesis 9 fully screwed therein. The retaining flange 55 (shown in FIG. 5C) sits on the internal bottom face of the acetabular cup prosthesis 9 once fully threaded in. The distal drive train shaft 35, the threaded tip 37 and the retaining flange 55 together form the prosthesis engaging interface 11. Also shown with more details in FIGS. 5A, 5B and 5C, the distal drive train shaft 35 is engaged into the U-shaped trough of the clamping slide 36. The clamping slide 36, having preferably four slide pins 22 (two on each side), moves along the axis of the distal drive train shaft 35 by sliding into slide grooves 21 on internal surfaces of the impactor body 8. The retaining flange 51 of the distal drive train shaft 35 contacts the proximal face of the clamping slide 36 and is pulled backward when the clamping slide 36 moves backward. The backward displacement of the distal drive train shaft 35 pulls the acetabular cup prosthesis 9 against the impactor nose 38. Once the pulling force has reached a certain level, friction forces between the internal bottom face of the acetabular cup prosthesis 9 and the front face of the impactor nose 38 prevent the cup prosthesis from moving or rotating.

Figure 4:
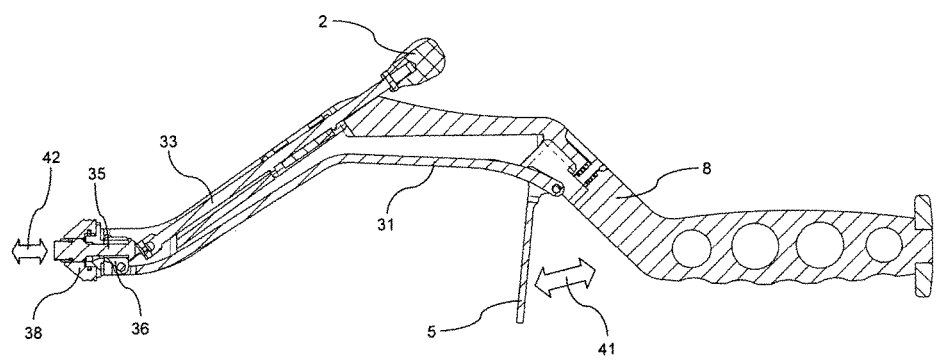
FIG. 4 is a cross-section view of the acetabular cup impactor in the opened position.

Referring now to FIG. 4, a cross-section view of the acetabular cup impactor is shown in the open position. Note that the acetabular cup prosthesis is not shown in this figure for clarity and to simplify the drawing. The clamping slide 36 is linked to the clamping handle 5 by a clamping lever 31. The three components are linked together with two pins 23a, 23b acting as hinges. Eccentric pins may be used (in this embodiment and the further embodiments herein described) to adjust the length of the hinges and therefore the force (tension) of the clamping. The rotation (41) of the clamping handle 5 away from the impactor body 8 induces movement of the clamping lever 31 which also induces movement of the clamping slide 36. The clamping slide 36 slides frontward (towards the tip of the cup impactor) and therefore releases the pulling force on the distal drive train shaft 35. The distal drive train shaft 35 can then be free to move frontward (42) and therefore releasing the friction forces between the cup prosthesis 9 and the impactor nose 38. In the open position, the distal drive train shaft 35 (and therefore the acetabular cup prosthesis 9 when mounted on the prosthesis engaging interface 11) is free to rotate when the positioning knob 2 of the drive train is rotated.

The rotation (41) of the clamping handle 5 in the opposite direction, towards the impactor body 8, induces a backward movement of the clamping slide 36 (towards the handle of the cup impactor) and therefore moves the distal drive train shaft 35 backward. The backward displacement of the distal drive train shaft 35 moves the acetabular cup prosthesis 9 against the impactor nose 38 until they contact each other. The elastic deformation of the clamping lever 31, acting like a spring, ensures a progressive and increasing pulling force on the distal drive train shaft 35 until the clamping handle 5 has reached its final backward position shown in FIG. 3. In the preferred embodiment, typical of an over center mechanism, the increase of the force given by the clamping lever 31 reaches a neutral point a little before the clamping handle 5 has reached its final backward position. Exceeding this neutral point, the force will decrease a little but also ensure that the clamping handle 5 stays in position against the impactor body 8 during impaction shocks.

Figure 5A:
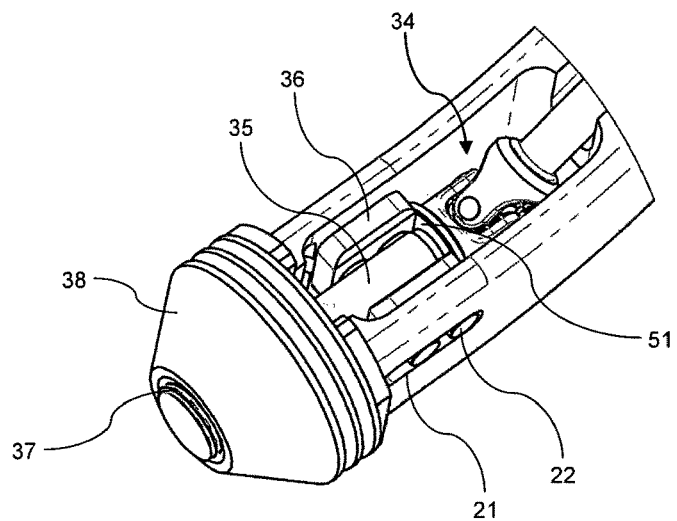
FIG. 5A is a detailed view of the distal end of the acetabular cup impactor.
Figure 5B:
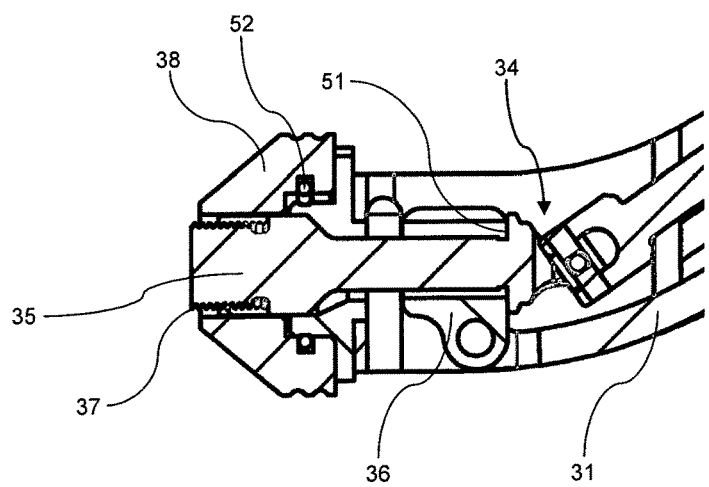
FIG. 5B is a detailed cross-section view of the distal end of the acetabular cup impactor.
Figure 5C:
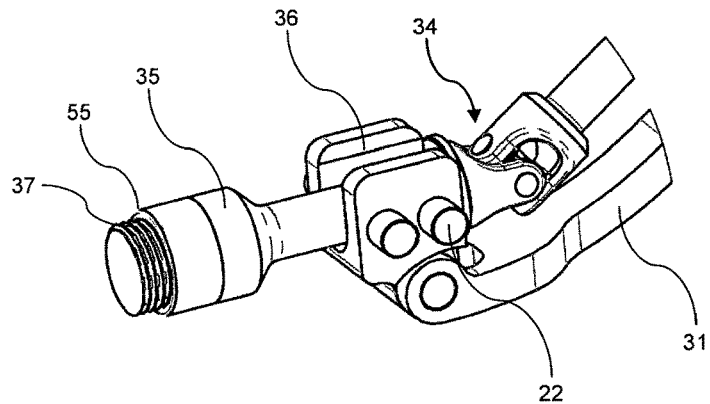
FIG. 5C is a partial view of the distal end of the acetabular cup impactor.

Referring to FIG. 5B, a cross-section view of the distal part of the acetabular cup impactor shows the impactor nose 38 having a C-ring 52 allowing it to be snapped on the distal tip of the impactor body 8. The impactor nose 38 can be further pulled apart from the impactor body for disassembling of the drive train assembly 71. In a typical situation, the profile of the impactor nose 38 is be adapted to the inner surface of the cup prosthesis 9. Several impactor noses 38 can be provided in a kit in order to accommodate different implants 9. In a further variant not shown in the figure, the distal portion of the impactor nose 38 may include an anti-rotation feature having a shape (square, hexagonal, etc.) that will match that of the cup prosthesis 9. During clamping, this feature engages into a corresponding feature of the cup 9, and therefore prevents rotation of the implant 1, 1', and 1". For clarity only, FIG. 5C shows the distal drive train shaft 35, the clamping slide 36 and the clamping lever 31 without the impactor body 8.

Figure 6A:
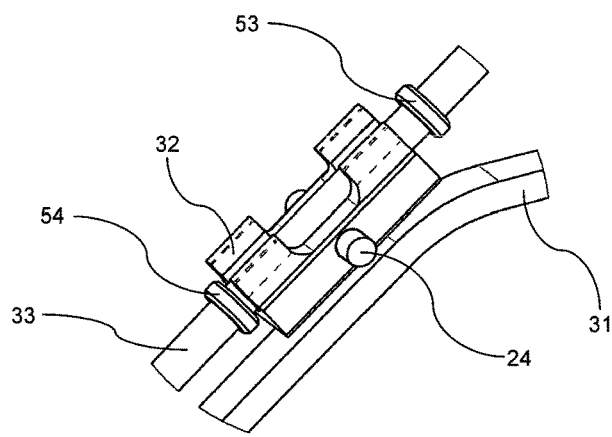
FIG. 6A is a partial view of the drive train bearing of the acetabular cup impactor.
Figure 6B:
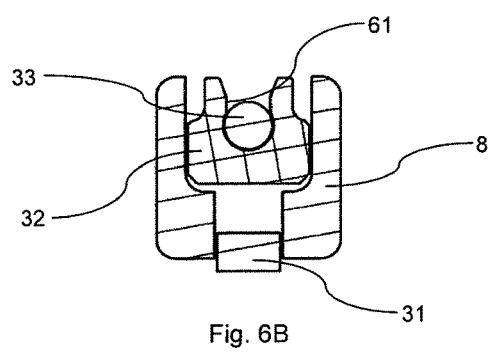
FIG. 6B is a cross-section view of the drive train bearing of the acetabular cup impactor.

Now referring to FIG. 6A, the fixation mechanism of the drive train is shown. The proximal drive train shaft 33 is snapped into the drive train bearing 32. A cross-section view of the drive train bearing 32 having a C-shaped opening with two elastic retaining lips 61 is shown in FIG. 6B. Once inserted, the drive train assembly 71, and therefore the proximal drive train shaft 33, can rotate and axially move into the drive train bearing 32. Two stops 53 and 54 limit the axial displacement of the shaft 33. The drive train bearing 32 is connected to the impactor body 8 through two bearing pins 24 which allows it to pivot. In the preferred embodiment, the drive train bearing 32 is made out of plastic.

Figure 7:
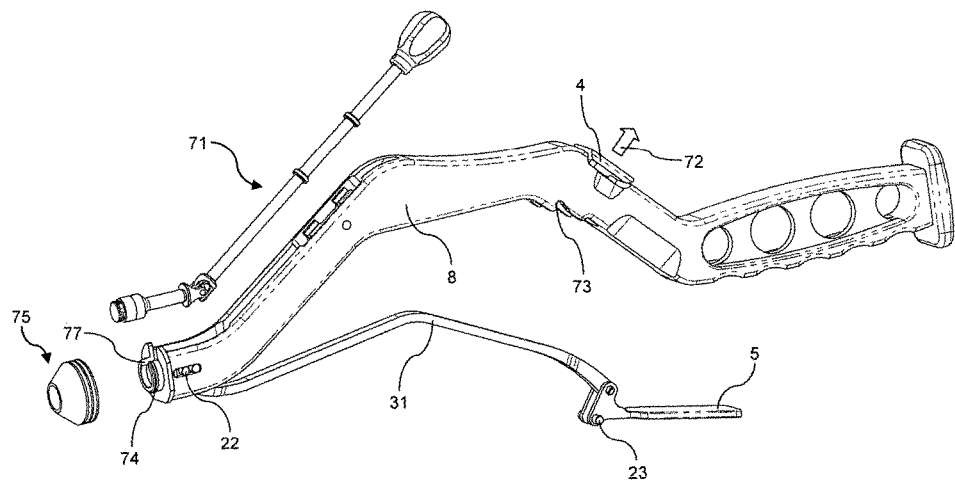
FIG. 7 is a perspective view of the acetabular cup impactor in the disassembled configuration.

Referring now to FIG. 7, a disassembled view of the acetabular cup impactor 1 is shown adapted for easier cleaning and sterilization of the instrument.

Figure 8:
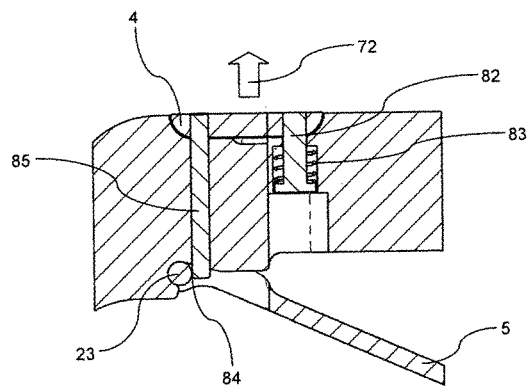
FIG. 8 is a detailed cross-section view of the handle release mechanism.

Referring now to FIG. 8 a detailed cross-section of the handle release mechanism is shown. By pulling up (72) the release handle actuator 4, the release pins 85 connected to the handle actuator clear the pivoting hole openings 73 where the handle pivoting pins 23 of the clamping handle 5 are maintained. It allows the clamping handle 5 to be disengaged from the impactor body, aided by internally disposed grooves 21 shown in dashed lines in the figure. The spring 83 mounted on the shaft 82 moves the release handle actuator 4 back on its initial down position. The clamping handle 5 and the clamping lever 31 may then be drawn out of the impactor body where the pins 22 exit the internal grooves and free the assembly. In order to avoid losing pieces, the clamping lever 31 stays connected to the clamping slide 36. The impactor nose 75 may also be pulled out of the impactor body 8. It will clear the U-shaped opening 77 which allows the distal drive train shaft 35 of the drive train assembly 71 to be removed. The complete drive train assembly 71 may then be drawn out of the impactor body 8 by pulling on it and unsnapping it from the drive train bearing 32.

For re-assembling the cup impactor, the clamping lever 31 and the clamping handle 5 are placed back into the impactor body 8. The handle pivoting pins 23 of the clamping handle 5 are then engaged into the pivoting hole opening 73. This action pushes the release pins 85 up until the handle pivoting pins 23 are fully engaged into the impactor body 8. The release pins 85 move then back into their initial position and lock (84) the handle pivoting pins 23. The drive train assembly 71 may then be snapped back into the drive train bearing 32 and replaced into the impactor body 8. The impactor nose 75 may also be snapped back onto the distal tip of the impactor body 8.

Figure 9A:
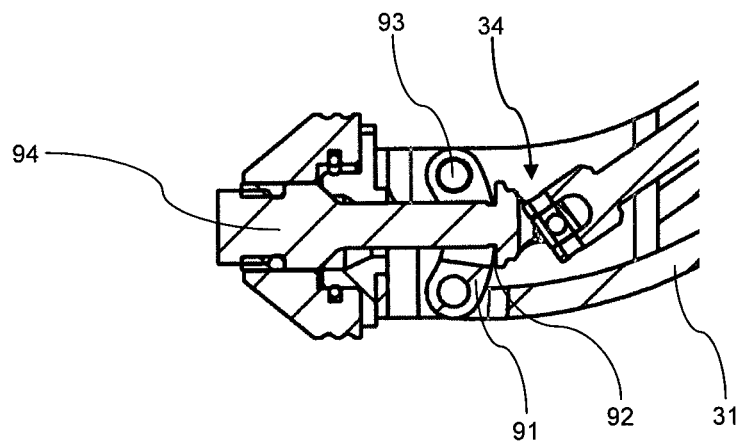
FIG. 9A is a detailed cross-section view of the distal end of a second embodiment of the acetabular cup impactor.

Referring now to FIG. 9A, in a second embodiment, a clamping slide 91 having a concave kidney bean shape is shown. Movement of the clamping lever 31 induced rotation of the clamping slide 91 around the pivoting pin 93. The retaining section 92 of distal drive train shaft 94, which slides on the concave face of the clamping slide 91, follows the movement of the clamping slide and is pulled backward. As described above, the backward displacement of the distal drive train shaft 94 locks the acetabular cup prosthesis against the impactor nose.

Figure 9B:
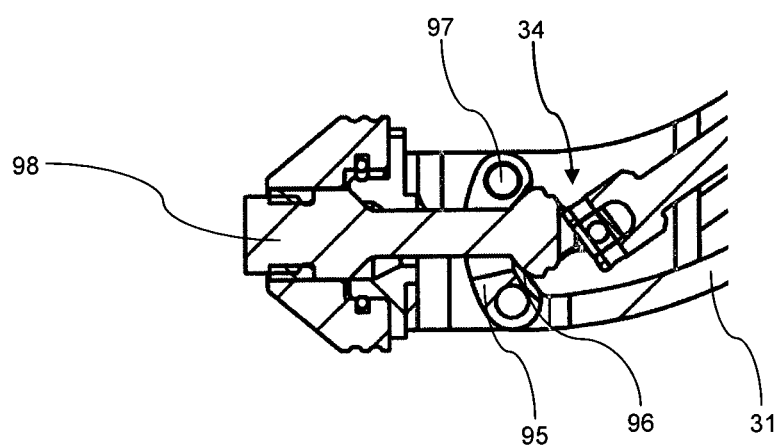
FIG. 9B is a detailed cross-section view of the distal end of a third embodiment of the acetabular cup impactor.

Referring now to FIG. 9B, in a third embodiment, a clamping slide 95 is shown having a convex kidney bean shape. Movement of the clamping lever 31 induced rotation of the clamping slide 95 around the pivoting pin 97. The spherical retaining section 96 of distal drive train shaft 98, which slides on the convex face of the clamping slide 95, follows the movement of the clamping slide and is pulled backward. As described above, the backward displacement of the distal drive train shaft 98 locks the acetabular cup prosthesis against the impactor nose.

Figure 10:
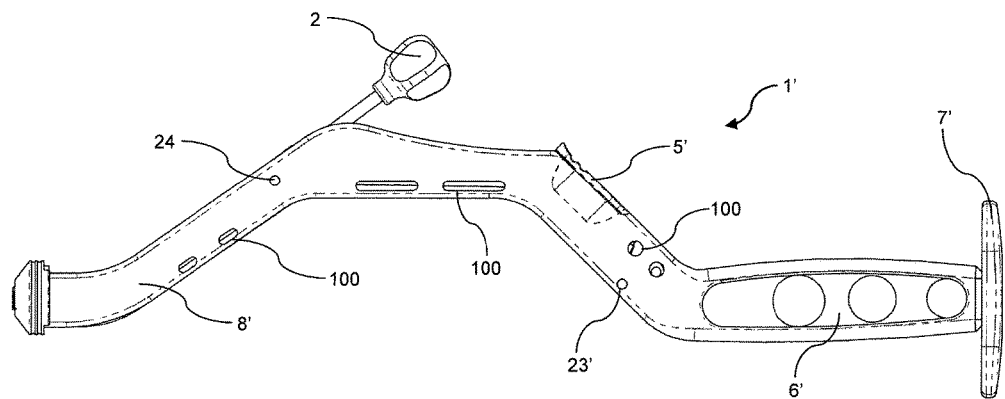
FIG. 10 is a top view of an alternate embodiment of the impactor of the invention.
Figure 11:
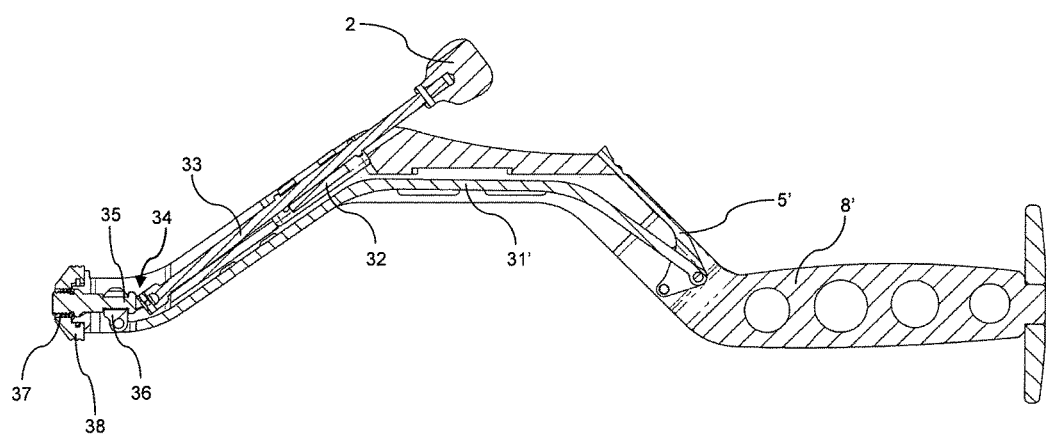
FIG. 11 is a cross-sectional view of the alternate embodiment of FIG. 10.
Figure 12:
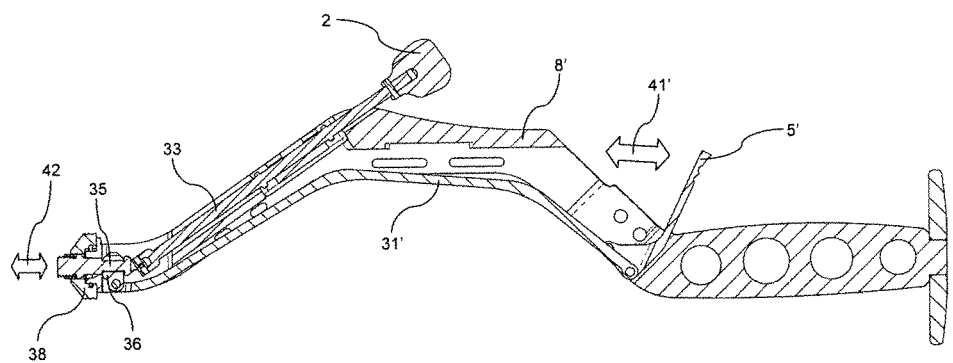
FIG. 12 is a cross-sectional view of the alternate embodiment of FIG. 10, with the lever released so as to release an impactor head.

Referring now to FIGS. 10, 11 and 12 a variant of the embodiment of FIGS. 2, 3 and 4 is shown in which the clamping handle 5' of the cup impactor 1' is located on the top of the impactor body 8'. Pulling on the clamping handle 5' releases the cup 9 (by moving the threaded tip 37 forward), and pushing on the clamping handle 5' locks the cup 9 (by moving the threaded tip 37 backward).

Figure 13:
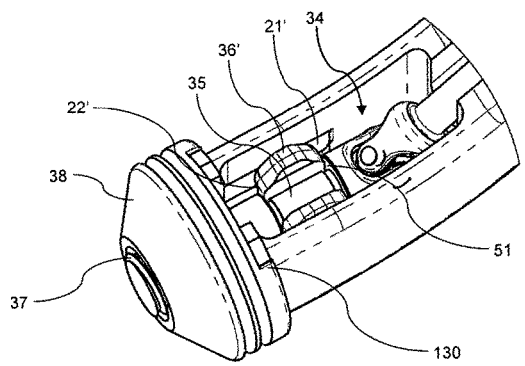
FIG. 13 is a perspective view of an alternate embodiment of the invention shown in FIG. 5A.
Figure 14:
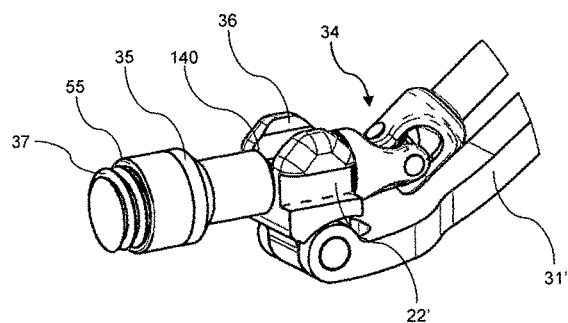
FIG. 14 is a partial, perspective view of elements of the alternate embodiment of the invention shown in FIG. 5A.

Referring now to FIGS. 13 and 14, different embodiment of FIGS. 5A and 5C where an additional retaining section 140 has been added to the distal drive shaft 35. This retaining section 140 contacts the distal face of the clamping slide 36' and is pushed frontward when the clamping slide 36' moves frontward. The frontward displacement of the distal drive train shaft 35 moves the cup away from the nose 38. In this embodiment, the clamping slide 36', having one groove 22' on each side, moves along the axis of the distal drive train shaft 35 by sliding onto the two rails 21' of the impactor body 8'. In this embodiment, the impactor nose 38 has one flange 130 on each side that contacts the lateral side of the distal end of the impactor body 8' in order to prevent it from rotating.

Figure 15:
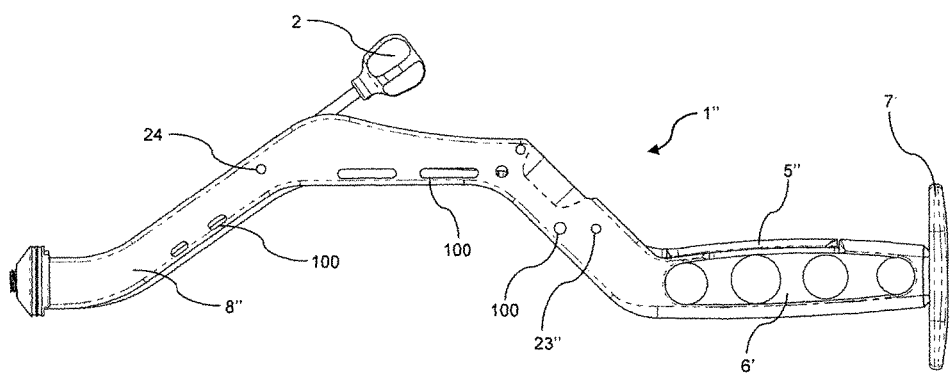
FIG. 15 is a top or plan view of a second alternate embodiment of the impactor of the invention.
Figure 16:
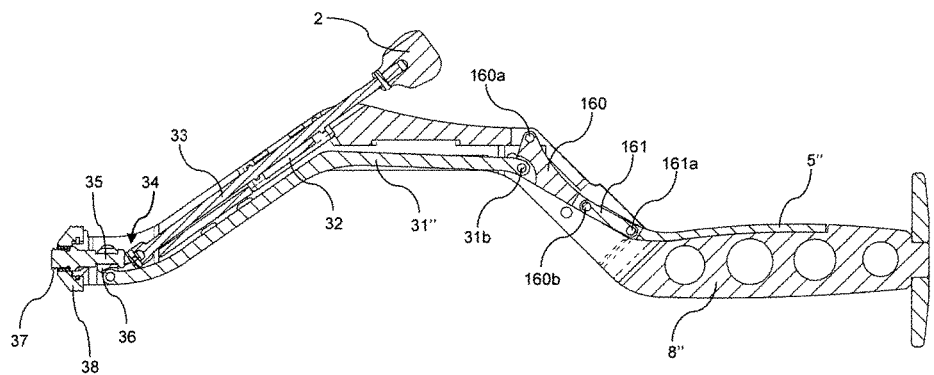
FIG. 16 is a cross-sectional plan view of the second alternate embodiment of the impactor of the invention in an unlocked position.
Figure 17:
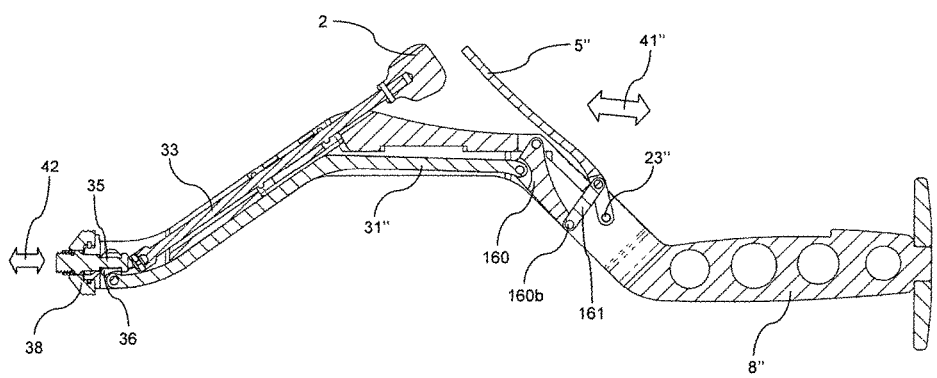
FIG. 17 is a cross-sectional plan view of the second alternate embodiment of the impactor of the invention in a locked position.

Referring now to FIGS. 15 to 17, a further embodiment of the invention 1" is shown having additional lever arm stages 160 and 161 which increases leverage and thereby reduces the force required on the clamping handle 5" to pull or clamp on the cup 9. FIG. 15 shows the side view of the cup impactor 1" with the clamping handle 5" in the closed position. FIG. 16 shows a cross section of this side view with the linkage made up of a first stage lever 160, pivotally connected via a pin 31b to the lever 31" and to pivot with respect to the housing 8" on a pin 160a, and to a second stage lever arm 161 via a pin 160b. The second stage lever 161 is in turn connected via a pin 161a to the clamping handle 5". The clamping handle 5" is pivotally connected to the housing 8" via pin 23". The assembly is shown in cross section in this figure in a lock or clamping position.

Referring in particular to FIG. 17, the impactor 1" is shown in cross section with the clamping handle 5" and levers connected thereto, in an open (unlocked or unclamped) position (release of the cup). It is evident that this configuration increases the leverage essentially by the length of the lever arms of lever arm stages 160 and 161 while not dramatically increasing the envelop required to operate the mechanism, thereby saving space while making it easier for the surgeon to clamp and unclamp a prosthesis 9 to the impactor nose 38.

In an advantage, the lever 31, 31', 31", activated by the clamping handle 5, 5', 5", pulls the distal drive train shaft with the clamping slide 36 (in order to lock the cup) that does not put any force on the universal joint or the proximal region of the drive train assembly 71, 71'. This increases the service life of the impactor of the invention.

The drive train assembly 71 may be replaced with alternative drive train assemblies 71' having an alternative prosthesis engaging surface 11' which is readily removable and replaceable.

Figure 18:
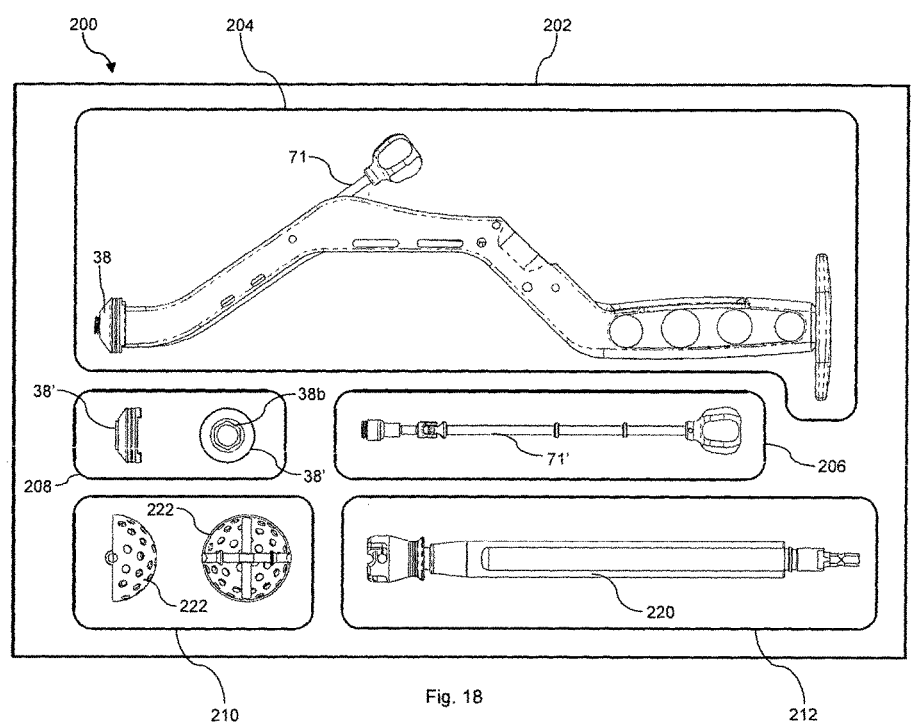
FIG. 18 is a plan view of a kit of the invention.

Referring now to FIG. 18, a surgical kit 200 includes: (a) a tool holder sterilization case 202 having compartments for holding elements needed to effect a given surgical intervention; (b) the impactor 1, 1', 1" of the invention; (c) at least one drive train assembly 71, 71'; (d) optionally, an additional impactor nose 38'. The kit 200 may further include: (e) a surgical reamer handle 220 for preparing the acetabulum for a prosthesis 9; and (f) a selection of acetabular reamers 222 for connection to and operation with the surgical reamer.

In another feature of the invention, the impactor nose 38 includes an anti-rotation feature 38b having a shape (of any cross section such as square, hexagon, or polygon) that interfacingly locks against a corresponding feature of a cup prosthesis 9.

Figure 19:
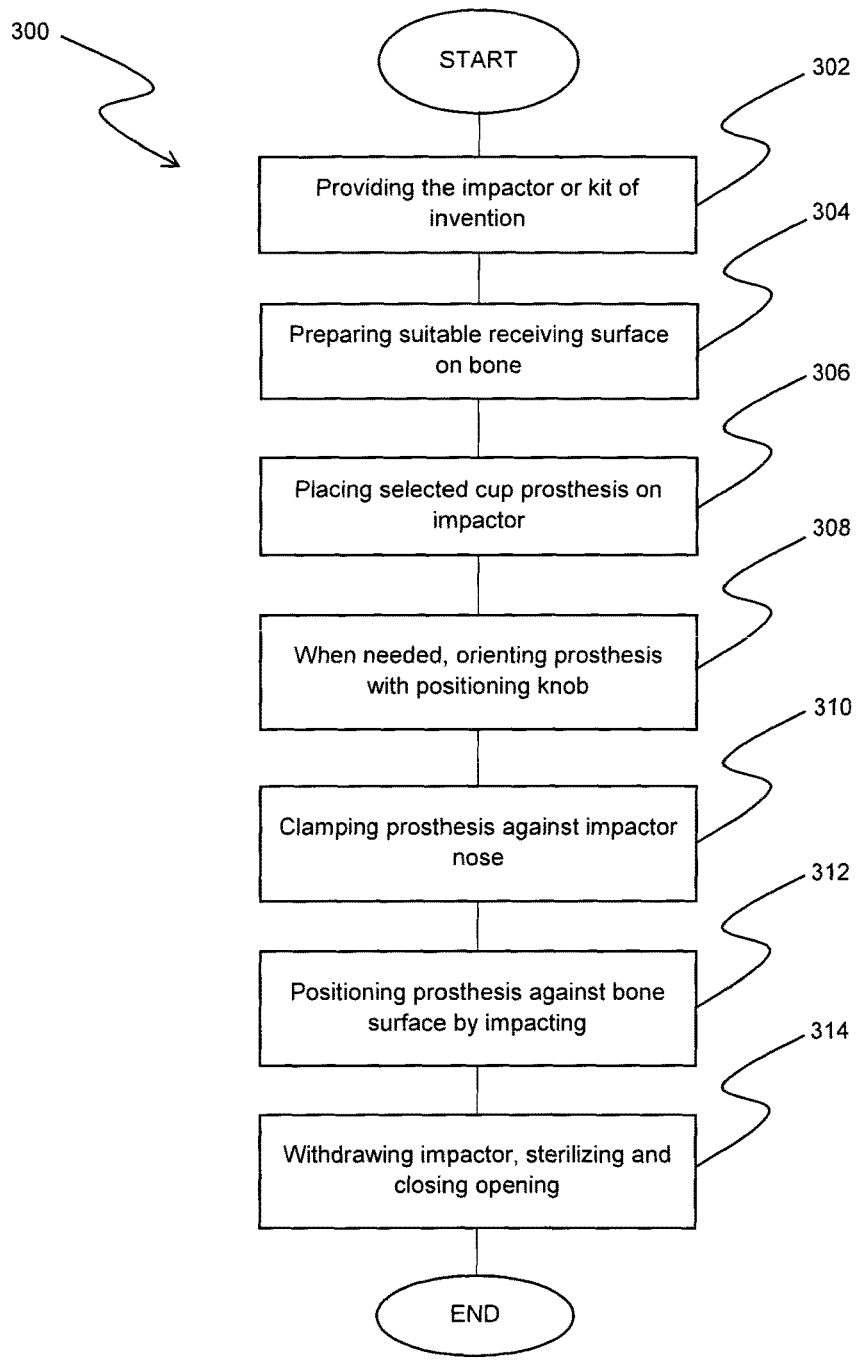
FIG. 19 is a flow chart of a method of the invention.

Referring now to FIG. 19, a surgical method 300 of the invention includes several steps. In a first step 302, the impactor 1, 1', 1" of the invention or the kit 200 of the invention is provided. In a second step 304, a suitable cup prosthesis receiving surface on a bone of a patient is prepared through a surgical opening. In a third step 306, a selected cup prosthesis is placed on an end of the impactor. In a fourth step 308, when needed, the cup prosthesis 9 is oriented with a positioning knob 2 of the impactor. In a fifth step 310, the prosthesis 9 is clamped against an impactor nose 38. In a sixth step 312, the cup prosthesis 9 is positioned in a proper orientation against the prepared bone surface by carefully and controllably impacting the impactor so as to advance the prosthesis in a final position against the bone. In a seventh step 314, the impactor is withdrawn and the opening is sterilized and closed.

An advantage of the present invention is to provide a simple device where the acetabular cup prosthesis 9 may be oriented first with the positioning knob 2 and then locked in an angular orientation against the impaction nose 38 by pulling on the clamping handle 5. The connection between the prosthesis is robust as the connection is made without any play or gaps therebetween, ensuring good support during impaction.

Another advantage of the invention is to provide a robust instrument by dissociating the orientation of the prosthesis made with the drive train assembly 71 and the locking of the prosthesis against the impactor nose. Prior art shows devices where the drive train assembly and its constituting universal joint are used to pull the prosthesis against the impactor nose. Advantageously, the present invention does not put any load on the universal joint when pulling the prosthesis against the impactor nose.

Another advantage of the invention is to provide a cup impactor 1, 1', 1" having a prosthesis engaging interface 11, which is part of the drive train assembly 71, thereby being easily exchangeable in order to match with different prosthesis interfaces.

Another advantage of the invention is to minimize the number of components and the risk that parts could be lost.

It will be understood that the particular method and devices embodying the invention are shown by way of illustration and not as a limitation of the invention. Although certain illustrative embodiments of the invention have been shown and described here, a wide range of modification, changes and substitutions is contemplated in the foregoing disclosure.

As will be appreciated by skilled artisans, the present invention may be embodied as a system, a device, or a method.

Moreover, the system contemplates the use, sale and/or distribution of any goods, services or information having similar functionality described herein.

The specification and figures should be considered in an illustrative manner, rather than a restrictive one and all modifications described herein are intended to be included within the scope of the invention claimed. Accordingly, the scope of the invention should be determined by the appended claims (as they currently exist or as later amended or added, and their legal equivalents) rather than by merely the examples described above. Steps recited in any method or process claims, unless otherwise expressly stated, may be executed in any order and are not limited to the specific order presented in any claim. Further, the elements and/or components recited in apparatus claims may be assembled or otherwise functionally configured in a variety of permutations to produce substantially the same result as the present invention. Consequently, the invention should not be interpreted as being limited to the specific configuration recited in the claims.

Benefits, other advantages and solutions mentioned herein are not to be construed as critical, required or essential features or components of any or all the claims.

As used herein, the terms "comprises", "comprising", or variations thereof, are intended to refer to a non-exclusive listing of elements, such that any apparatus, process, method, article, or composition of the invention that comprises a list of elements, that does not include only those elements recited, but may also include other elements such as those described in the instant specification. Unless otherwise explicitly stated, the use of the term "consisting" or "consisting of" or "consisting essentially of" is not intended to limit the scope of the invention to the enumerated elements named thereafter, unless otherwise indicated. Other combinations and/or modifications of the above-described elements, materials or structures used in the practice of the present invention may be varied or adapted by the skilled artisan to other designs without departing from the general principles of the invention.

The patents and articles mentioned above are hereby incorporated by reference herein, unless otherwise noted, to the extent that the same are not inconsistent with this disclosure.

Other characteristics and modes of execution of the invention are described in the appended claims.

Further, the invention should be considered as comprising all possible combinations of every feature described in the instant specification, appended claims, and/or drawing figures which may be considered new, inventive and industrially applicable.

Additional features and functionality of the invention are described in the claims appended hereto. Such claims are hereby incorporated in their entirety by reference thereto in this specification and should be considered as part of the application as filed.

Multiple variations and modifications are possible in the embodiments of the invention described here. Although certain illustrative embodiments of the invention have been shown and described here, a wide range of changes, modifications, and substitutions is contemplated in the foregoing disclosure. While the above description contains many specific details, these should not be construed as limitations on the scope of the invention, but rather exemplify one or another preferred embodiment thereof. In some instances, some features of the present invention may be employed without a corresponding use of the other features. Accordingly, it is appropriate that the foregoing description be construed broadly and understood as being illustrative only, the spirit and scope of the invention being limited only by the claims which ultimately issue in this application.

What is claimed is:

1. A cup impactor (1, 1', 1") adapted to assist a surgeon in controlling implantation of a cup prosthesis (9), the impactor having:
   (a) an impactor body (8) having on its proximal end, an impaction plate (7) connected thereto, and an impactor handle (6) formed thereon for handling by the surgeon and on its distal end, an impactor nose support portion;
   (b) a drive train assembly (71) provided with a universal joint (34) linking a proximal and distal end thereof, the assembly having a prosthesis engaging interface (11) at the distal end thereof, and a positioning knob (2) formed on the proximal end, the assembly (71) comprising a distal drive train shaft (35) received and rotatably mounted in a slide (36) interfacing with the body (8);
   (c) an impactor nose (38) having a distal interface which interfaces with a portion of a proximal surface of an impactor cup prosthesis (9), the impactor nose for mounting on the distal end of the impactor body (8), through which the prosthesis engaging interface (11) extends; and
   (d) a clamping handle (5), which, via the slide (36), releasably connects to the drive train assembly at a distal portion thereof at a location distal to a distal-most universal joint and is adapted to pull the distal portion of the drive train assembly (71) and therefore any cup prosthesis (9) attached to the engaging interface (11) against the impactor nose (38).

2. The cup impactor (1, 1', 1") of claim 1, wherein further the pulling action acts on a distal drive train shaft (35) of the drive train assembly (71), thereby avoiding straining a proximal portion of the drive train assembly (71).

3. The cup impactor (1, 1', 1") of claim 2, wherein at least one additional lever arm is connected between the lever (31) and the clamping handle (5) in order to increases leverage and thereby reduces the force needed on the clamping handle (5) when pulling on the cup.

4. The cup impactor (1, 1', 1") of claim 1, wherein a lever (31) is activated by the clamping handle (5) draws up and secures the prosthesis (9) against the impactor nose (38) to prevent rotation thereof.

5. The cup impactor (1, 1', 1") of claim 4, wherein the lever (31) is attached to a clamping slide (36) which engages with a feature of the distal drive train shaft (35) to pull the shaft thereby locking a prosthesis (9) on the impactor nose (38) when the prosthesis is installed on the distal end of the impactor.

6. The cup impactor (1, 1', 1") of claim 4, further including a release assembly having a release handle actuator (4), the release assembly being movable by the actuator (4) in a position for retaining and a position for releasing the clamping handle (5) and lever (31), the releasing facilitating cleaning and sterilization of the instrument.

7. The cup impactor (1, 1', 1") of claim 1, wherein the proximal and distal ends of the drive train assembly (71) are linked together by a universal joint (34).

8. The cup impactor of claim 7, wherein the clamping handle (5) initiates a pulling distal to the universal joint (34) so as to avoid straining the universal joint and the proximal portion of the drive train assembly (71).

9. The cup impactor (1, 1', 1") of claim 1, wherein the prosthesis engaging interface (11) comprises a thread adapted to engage with a corresponding thread of the prosthesis (9).

10. The cup impactor (1, 1', 1") of claim 1, wherein the drive train assembly (71) is enclosed and maintained in the impactor body (8) by at least one drive train bearing (32).

11. The cup impactor (1, 1', 1") of claim 1, wherein when the clamping handle (5) is in the open position, rotation of the positioning knob (3) rotates the cup prosthesis (9).

12. The cup impactor (1, 1', 1") of claim 1, wherein the impactor body (8) is C-shaped in order to minimize the invasiveness of the surgery by clearing anatomical structures.

13. The cup impactor (1, 1', 1") of claim 1, wherein an axis of the impactor handle (6) is approximately aligned with the axis of the prosthesis engaging interface (11).

14. The cup impactor (1, 1', 1") of claim 1, wherein the impactor nose (38) includes an anti-rotation feature (38b) having a shape that interfacingly locks against a corresponding feature of a cup prosthesis (9).

15. The cup impactor (1, 1', 1") of claim 1, wherein the drive train assembly (71) having a first prosthesis engaging surface (11) is readily removable and replaceable with an alternate drive train assembly having a second prosthesis engaging surface (11').

16. The cup impactor (1") of claim 1, wherein further lever arm stages (160, 161) increase leverage while minimizing an envelope of operation of the impactor.

* * * * *